US00PP21534P3

(12) United States Plant Patent
Kopan

(10) Patent No.: US PP21,534 P3
(45) Date of Patent: Nov. 30, 2010

(54) PEAR TREE NAMED 'ROKSOLANA'

(50) Latin Name: ***Pyrus communis* L.**
Varietal Denomination: Roksolana

(75) Inventor: Volodymyr Kopan, Novosilky (UA)

(73) Assignee: SNC Elaris, Angers (FR)

( * ) Notice: Subject to any disclaimer, the term of this patent is extended or adjusted under 35 U.S.C. 154(b) by 222 days.

(21) Appl. No.: 12/074,086

(22) Filed: Feb. 28, 2008

(65) Prior Publication Data

US 2009/0222960 P1 Sep. 3, 2009

(51) Int. Cl.
*A01H 5/00* (2006.01)

(52) U.S. Cl. ..... Plt./176

(58) Field of Classification Search ..... Plt./176
See application file for complete search history.

(56) References Cited

PUBLICATIONS

GTITM UPOVROM Citation for 'Roksolana' as per QZ PBR 20050502; Mar. 17, 2005.*

GTITM UPOVROM Citation for 'Roksolana' as per FR NLI 7000330; application filing No. 1017666; Apr. 7, 2005.*

* cited by examiner

*Primary Examiner*—Kent L Bell
(74) *Attorney, Agent, or Firm*—Michelle Bos

(57) ABSTRACT

A new pear tree named 'Roksolana' is disclosed. Fruit of 'Roksolana' is notable for its excellent eating quality-the fruit is firm and somewhat juicy, with high sugar and acid levels that give the fruit a complex and durable aroma and flavor. 'Roksolana' pears are harvested relatively late in the season, and have been found to store well over long periods. Once taken out of storage, 'Roksolana' pears are slow to mature and have a long shelf life.

5 Drawing Sheets

Latin name:
*Pyrus communis* L.
Variety denomination: 'Roksolana'.

BACKGROUND OF THE VARIETY

'Roksolana' is a product of a controlled breeding program carried out by the inventor at Lviv, Western Ukraine. 'Roksolana' was one of several seedlings resulting from a cross made in 1961 of female parent 'Parizhanka' (not patented) and male parent 'Beurre Bosc' (not patented). 'Parizhanka' was selected for its winter hardiness, tolerance to scab, and very good storageability. 'Beurre Bosc' was selected for its productivity, late blooming, and good eating quality. 'Roksolana' was grafted onto rootstock in 1964 at Lviv, and fruit of the variety was first observed in 1969. After several years of observation, 'Roksolana' was found to exhibit desireable characteristics, and was selected for further evaluation. In the early 1990s, 'Roksolana' was asexually propagated by grafting, and planted in an experimental orchard in France. Second generation trees were planted in 2000 and 2002, and third generation trees were planted in 2006. 'Roksolana' has been observed to remain true to type over successive asexually propagated generations.

BRIEF DESCRIPTION OF THE VARIETY

'Roksolana' was selected for its suitability as a commercial pear tree. In field trials, 'Roksolana' has been found to show resistance to fungus, especially scab (*Venturia pirina*). Fruit of 'Roksolana' is notable for its excellent eating quality - the fruit is firm and somewhat juicy, with high sugar and acid levels that give the fruit a complex and durable aroma and flavor. The fruit of 'Roksolana' is harvested relatively late in the season, and has been found to store well over long periods. Once taken out of storage, 'Roksolana' is slow to mature and has a long shelf life.

BRIEF DESCRIPTION OF THE PHOTOGRAPHS

Figure 1:
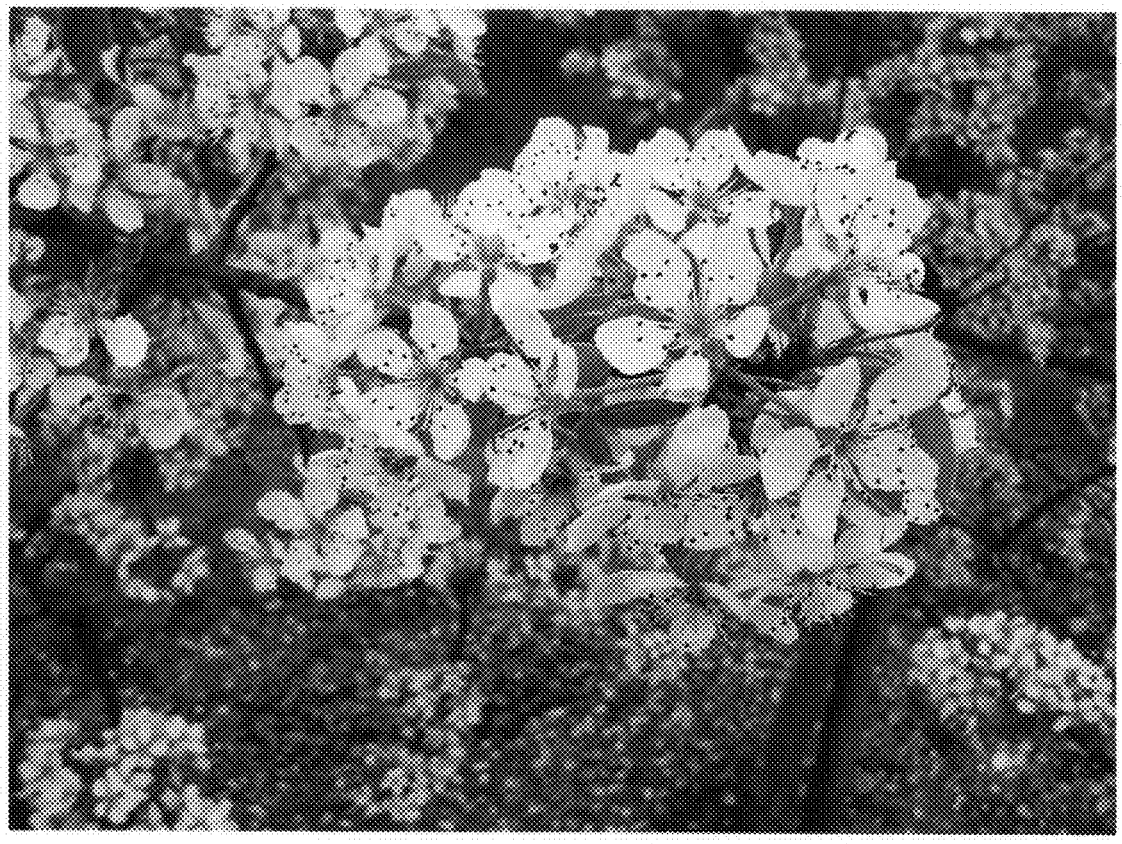
FIG. 1 shows the flowers of the new variety.
Figure 2:
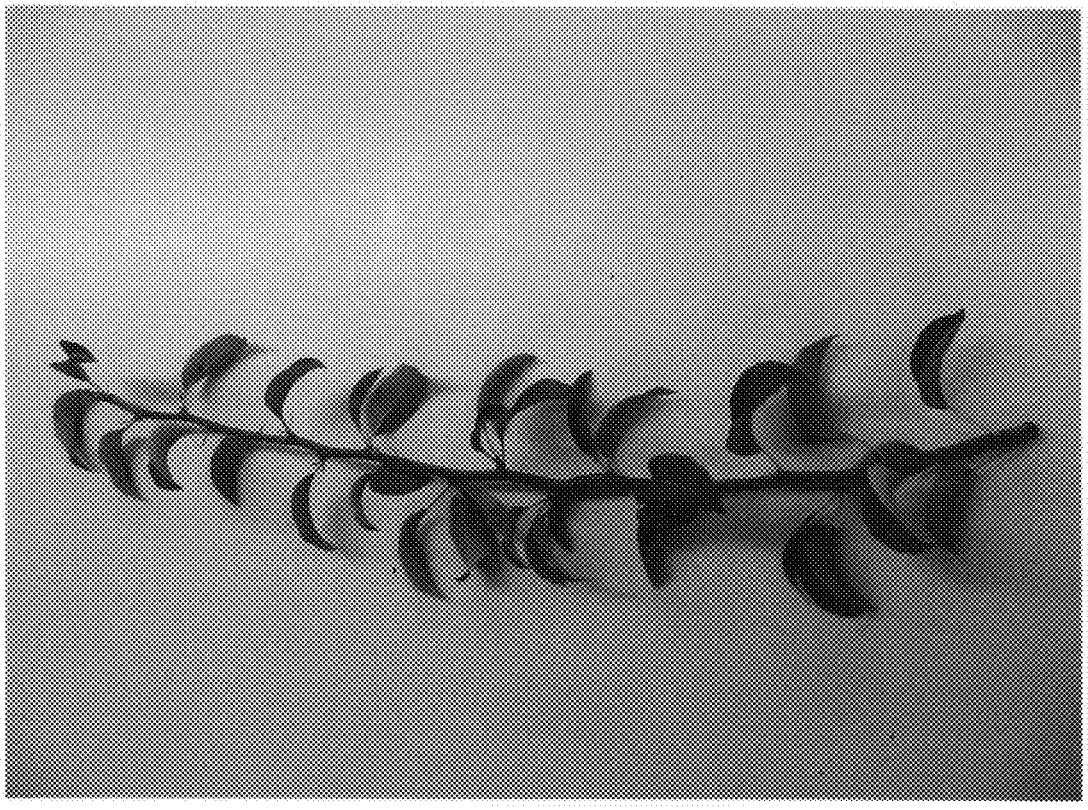
FIG. 2 shows the branch and leaves of the new variety.
Figure 3:
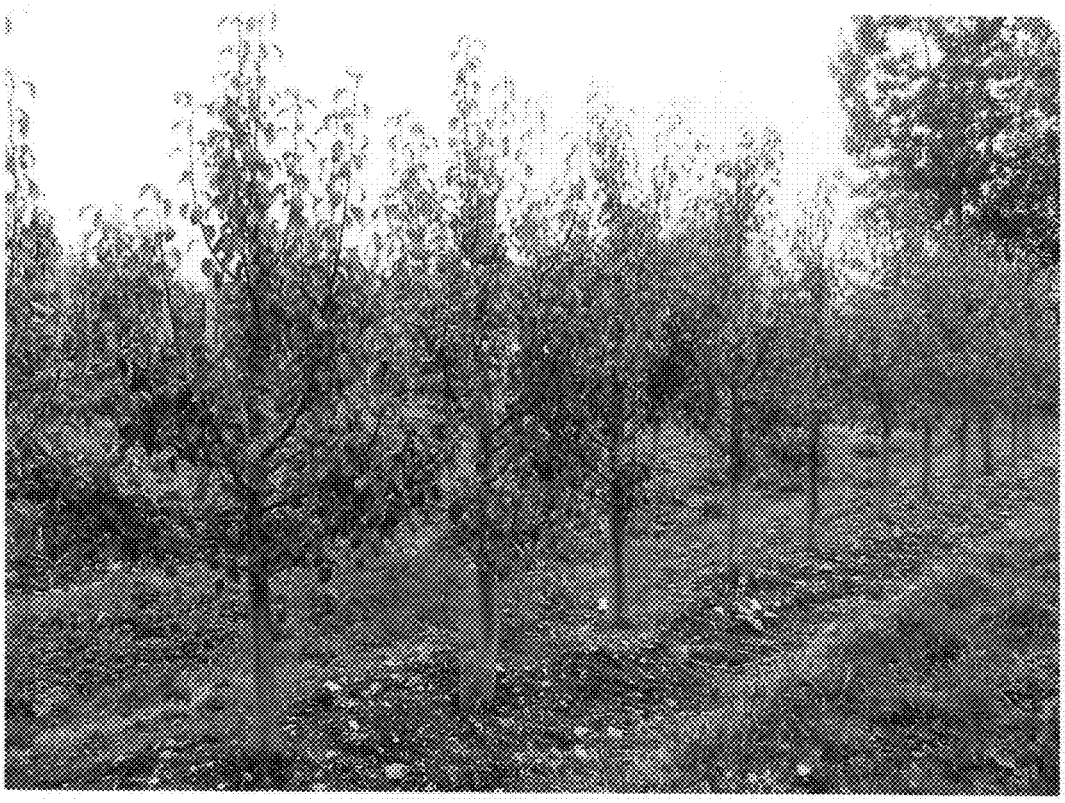
FIG. 3 shows trees of the new variety.
Figure 4:
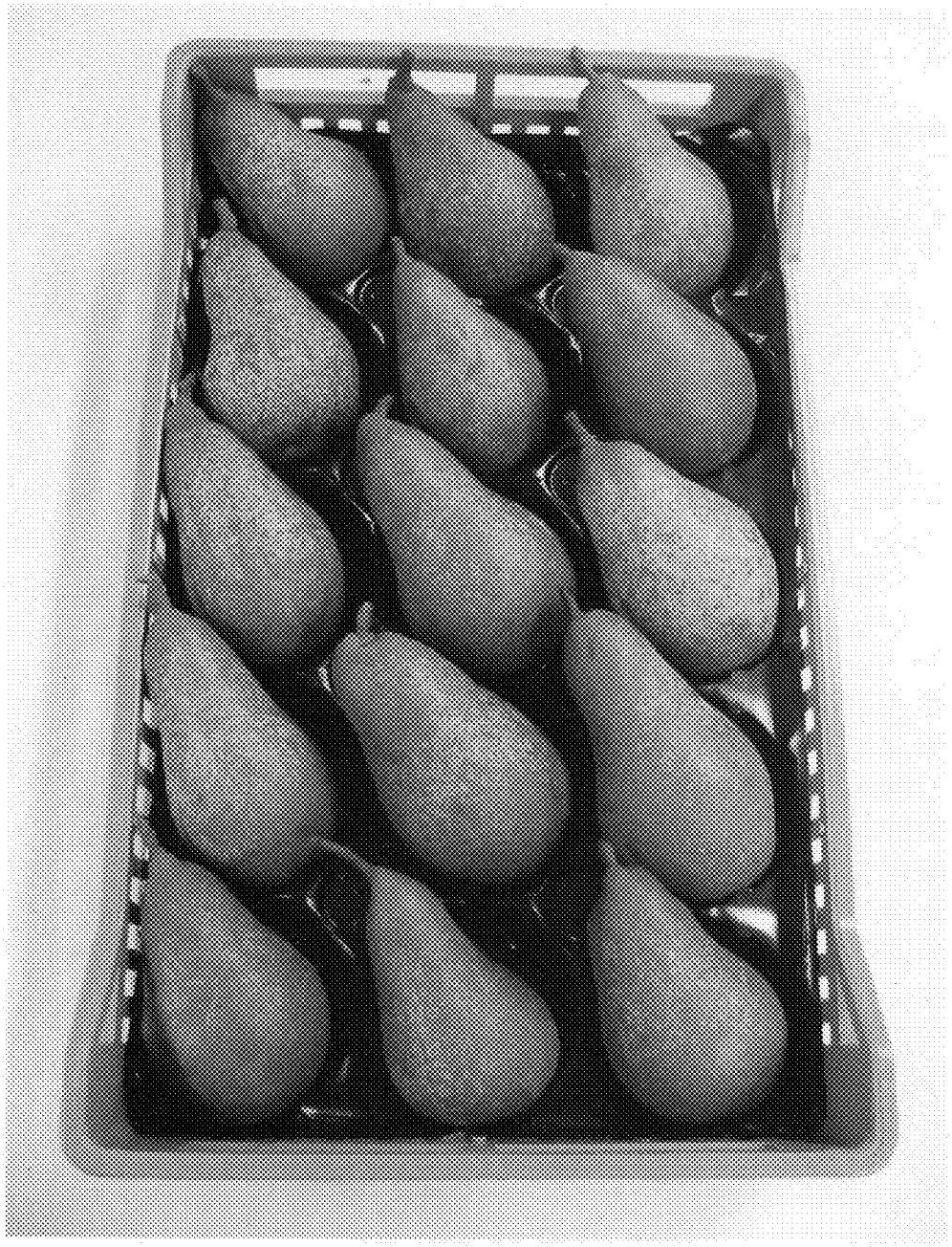
FIG. 4 shows fruit of the new variety after 2 months of storage.
Figure 5:
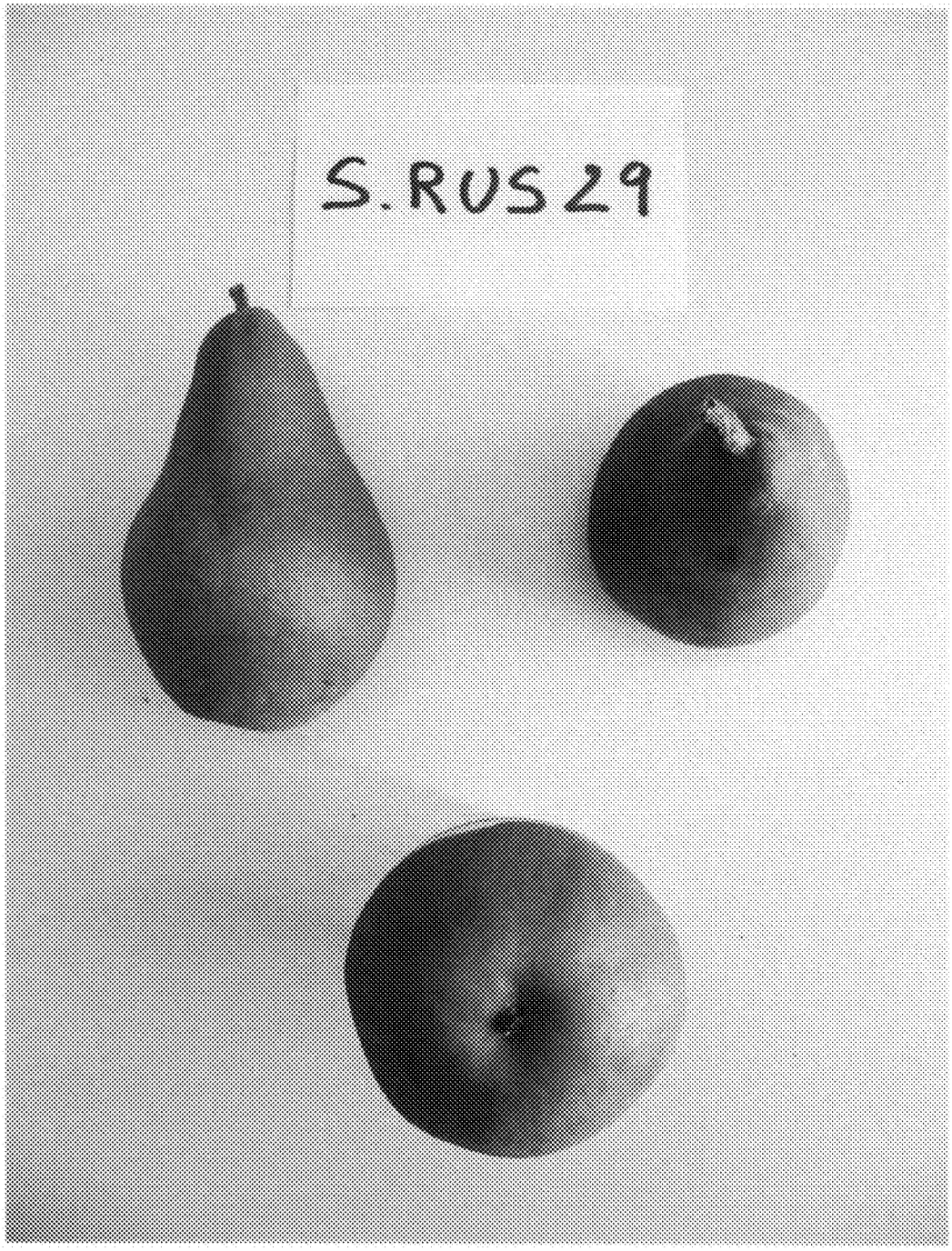
FIG. 5 shows detail of fruit of the new variety after 2 months of storage.

The colors of this illustration may vary with lighting conditions and, therefore, color characteristics of this new variety should be determined with reference to the observations described herein, rather than from these illustrations alone.

DETAILED BOTANICAL DESCRIPTION OF THE VARIETY

The following detailed botanical description is based on observations made during the 2007 and 2010 growing seasons near Angers, France, of trees planted in 2000 on 'BA29' rootstock (not patented). All colors are described according to The Royal Horticultural Society Colour Chart. It should be understood that the characteristics described will vary somewhat depending upon cultural practices and climatic conditions, and will vary with location and season. Quantified measurements are expressed as an average of measurements taken from a number of individual plants of the new variety.

The measurements of any individual plant, or any group of plants, of the new variety may vary from the stated average.

Tree: 'Roksolana' is a vigorous and upright growing tree that does well on dwarfing rootstock to control growth; this variety has shown good compatibility on Quince C rootstock. 'Roksolana' shows strong winter hardiness, and does well in the field, where it has shown tolerance to scab. This trait is believed to come from its female parent 'Parizhanka'.

*Vigor.*—Very vigorous.
*Branching.*—Very strong.
*Habit.*—Semi-upright.
*Size*—Height, 2.90 m; Spread 2.80 m.
*Trunk diameter.*—(*at* 30 *cm above the graft union*).—66 mm.
*Bark color.*—Grey 202C.
*Bark texture.*—Tender, smooth.
*Winter hardiness.*—Very hardy.

Branch (fruiting branches located at around 1 m above the graft union):

*Length.*—130 em.
*Diameter* (*at* 10 *cm from trunk*).—31 mm.
*Branch color.*—Brown N199C.
*Crotch angle.*—40° from vertical.

One year old shoot:

*Length.*—Avg. 40 cm.
*Pubescence intensity.*—Weak.
*Thickness.*—Thin, 6 mm.
*Type of growth.*—Wavy (similar to 'Beurre Bose').
*Internode length.*—Medium, avg. 28 mm (similar to 'Beurre Hardy' (not patented).
*Predominant color on sunny side.*—Dark Brown 200C.
*Shape of vegetative buds.*—Oval.
*Shape of apex of vegetative buds.*—Obtuse (similar to 'Passe Crassane' (not patented)).
*Vegetative bud color.*—Dark brown 200B.
*Size of bud support.*—Large.
*Position of vegetative buds in relation to shoot.*—Markedly divergent (similar to 'Conference' (not patented).
*Number of lenticels.*—Medium, avg. 4/cm$^2$ (similar to 'Williams' (not patented)).

Flowers: 'Roksolana' blooms around April 1 in the Loire Valley, France. Full bloom of 'Roksolana' is reached just after 'Williams' (April 10 in Loire Valley, France, 2007 growing season). Blossoms are abundant, so careful thinning of the variety is important to ensure adequate fruit set. 'Roksolana' produces fruit on spurs as well as on one year old shoots. Productivity is average, and the variety can exhibit a tendency to biannual bearing when not managed properly.

*Location of buds.*—On spurs and long shoots.
*Quantity of buds per spur.*—1 to 2.
*Bud size.*—Diameter medium, 10 mm; length medium, 10 mm.
*Bud shape.*—Round.
*Bud color.*—Dark brown 200C.
*Flower color* (*balloon stage*).—White 155D.
*Diameter of open flower.*—Large, 32 mm.
*Flower depth.*—13 mm.
*Relative position of petal margin.*—Not touching.
*Quantity of flowers per cluster.*—5 to 7.

Petals:

*Quantity per flower.*—5.
*Shape.*—Ovate.
*Length.*—Medium, 12 mm.
*Width.*—Medium, 7 mm.
*Apex.*—Round.
*Base.*—Conical-pointed.
*Margin.*—Smooth.
*Color.*—Upper and lower surfaces white N155D.

Pistils:

*Length.*—Long, 17 mm.
*Color.*—Yellow green 149D.

Anthers:

*Quantity.*—Numerous, 18 per flower.
*Size.*—Medium, length 2.5 mm.
*Pollen.*—Present.
*Pollen color.*—Yellow 4B.

Stigma:

*Size.*—Medium, diameter 0.5 mm.
*Color.*—Yellow-green 145C.

Style:

*Size.*—Long, 12 mm.
*Color.*—Yellow-green N 144D.

Ovary:

*Size.*—Long, 2.5 mm.
*Color.*—Green 134A.

Pedicel:

*Length.*—Very long, 24 mm.
*Diameter.*—Thin, 1.2 mm.
*Color.*—Green-yellow 145B.

Sepals:

*Quantity.*—5.
*Color.*—Upper surface light yellow-brown 163B; lower surface yellow green 145B.
*Length.*—Very long, 4 mm.
*Width.*—Avg. 3 mm.
*Shape.*—Conical pointed.
*Apex.*—Narrow.
*Margin.*—Smooth.
*Attitude of sepals in relation to corolla.*—Recurved.

Leaves:

*Shape.*—Elliptic.
*Apex.*—Acuminate.
*Base shape.*—Cuneate.
*Length.*—Medium, avg. 52 mm.
*Width.*—Medium, avg. 29 mm.
*Length/width ratio.*—Medium.
*Margin.*—Bluntly to sharply serrate.
*Curvature of longitudinal axis.*—Strong (similar to 'Contesse de Paris' (not patented)).
*Color of upper surface.*—Dark green 141A.
*Color of lower surface.*—Green 139C.
*Attitude in relation to shoot.*—Outward (similar to 'Doyenne du Cornice' (not patented)).

Petiole:

*Length.*—Medium, avg. 33 mm (Similar to 'Beurre Hardy').
*Stipules.*—Present; color yellow green 145A; sword shaped; long, 12 mm; narrow, avg. 0.5 mm; apex acute.
*Distance of stipules from basal attachment of petioles.*—Short.
*Color.*—Light yellow-brown 160B.

Fruit:

The fruit of 'Roksolana' is similar in appearance to 'Beurre Bosc,' although slightly more elongated and more narrow around the calyx. It is 25% to 50% russeted, depending on the growing conditions. The stalk of 'Roksolana' is thicker and shorter than 'Beurre Bosc,' and the fruit of 'Roksolana' is on average larger than 'Beurre Bosc.' 'Roksolana' has a unique eating quality. The flesh is very firm for a pear, moderately juicy, and with a fine texture. 'Roksolana' has a high level of sugar and acidity, combined with a complex aroma.

*Quantity per cluster.*—2 to 3.
*Length.*—Medium to long, 120 mm.
*Maximum diameter.*—Medium, 71 mm.
*Ratio of length to diameter.*—Medium to large.
*Position of maximum diameter.*—Slightly towards calyx.
*Shape.*—Rhomboidal.
Weight.—Medium, 200 g.
*Symmetry in longitudinal section.*—Slightly asymmetric.
*Profile of sides.*—Concave to straight.
*Ground color of skin.*—Green 145B at harvest, turning light yellow 2C after storage.
*Skin texture.*—Granulous.
*Relative area of overcolor.*—Absent to very small.
*Relative area of russet around the eye basin.*—Large (similar to 'Conference').
*Relative area of russet on cheeks.*—Medium to large.
*Relative area of russet on stalk attachment.*—Large (similar to 'Beurre Hardy').
*Length of stalk.*—Short to medium, 15 mm.
*Thickness of stalk.*—Medium, 5 mm.
*Curvature of stalk.*—Very weak.
*Attitude of stalk in relation to axis of fruit.*—Oblique (similar to 'Doyenne du Cornice').
*Stalk color.*—Yellow brown N167A.
*Attitude of sepals at harvest.*—Erect (similar to 'Conference').
*Eye basin.*—Present.
*Depth of eye basin.*—Shallow, avg. 4 mm.
*Width of eye basin.*—Narrow, avg. 26 mm.
*Flesh texture.*—Fine.
*Firmness of flesh.*—Firm.
*Aroma.*—Complex.
*Juiciness.*—Medium.
*Shape of seeds.*—Ovate.
*Quantity of seeds per fruit.*—Avg. 8.
*Seed length.*—Avg. 8 mm.
*Seed width.*—Avg. 5 mm.
*Seed color.*—Purple brown 166A.

Harvest:

*Time for harvest.*—Very late (4 weeks after 'Conference'), October 12 in the 2009 growing season.
*Time of maturity for consumption.*—Very late.
*Yield.*—Medium; 24 kg/tree on 'BA29' rootstock (2500 trees per hectare, in $5^{th}$ leaf).
*Use.*—Fresh market.
*Disease and pest resistance/tolerance.*—None observed.

Storage: The storageability of 'Roksolana' is very good. It can be stored 2 to 3 months longer than 'Beurre Bose' under the same conditions. After storage, 'Roksolana' matures slowly, requiring at least 3 months in storage plus 2 weeks at 18° C. before being ready to eat. Humidity must be managed carefully during the maturing period in order to prevent dehydration. Once mature, 'Roksolana' pears exhibit a remarkably long shelf life.

TABLE 1

Comparison after 90 Days of Air Storage at −0.5° C.

| Variety | 'Beurre Bosc' | 'Roksolana' | 'Conference' |
|---|---|---|---|
| Firmness at harvest | 6 kg | 7 kg | 6 kg |
| Firmness after storage | 3.9 kg | 5.4 kg | 4.1 kg |
| Maturing time at 18° C. | 6 days | 17 days | 10 days |
| Shelf life after maturing | 7 days | 17 days | 10 days |

I claim:

1. A new and distinct pear tree substantially as described and illustrated herein.

* * * * *